US005464565A

United States Patent [19]

Hamann et al.

[11] Patent Number: 5,464,565
[45] Date of Patent: Nov. 7, 1995

[54] PROCESS FOR THE PREPARATION OF HIGHLY CONCENTRATED FREE-FLOWING AQUEOUS SOLUTIONS OF BETAINES

[75] Inventors: Ingo Hamann, Bad Orb; Hans-Jürgen Köhle, Schluchtern; Winfried Wehner, Neuhof, all of Germany

[73] Assignee: Witco Surfactants GmbH, Steinau an der Strasse, Germany

[21] Appl. No.: 321,141

[22] Filed: Oct. 11, 1994

[30] Foreign Application Priority Data

Oct. 8, 1993 [DE] Germany .................. 43 34 467.4

[51] Int. Cl.$^6$ .................. C11D 1/90; C07D 209/12
[52] U.S. Cl. .................. 252/546; 252/DIG. 7; 562/553; 554/52; 554/68
[58] Field of Search .................. 252/546, DIG. 7; 562/553; 554/52, 68

[56] References Cited

U.S. PATENT DOCUMENTS

| | | | |
|---|---|---|---|
| 3,225,074 | 12/1965 | Cowen et al. | 554/52 |
| 4,246,131 | 1/1981 | Lohr | 252/153 |
| 4,357,421 | 3/1983 | Rubin et al. | 252/153 |
| 4,497,825 | 2/1985 | Bade | 524/556 |
| 4,832,871 | 5/1989 | Bade | 252/546 |
| 4,861,517 | 9/1989 | Bade | 252/546 |
| 5,354,906 | 10/1994 | Weitemeyer et al. | 554/52 |

FOREIGN PATENT DOCUMENTS

| | | |
|---|---|---|
| 0353580 | 2/1990 | European Pat. Off. . |
| 3613944 | 8/1987 | Germany . |
| 3726322 | 12/1988 | Germany . |

*Primary Examiner*—Paul Lieberman
*Assistant Examiner*—E. Harriman
*Attorney, Agent, or Firm*—Scully, Scott, Murphy & Presser

[57] ABSTRACT

The invention relates to a process for the preparation of highly concentrated free-flowing aqueous solutions of betaines, which is characterized in that at least one of the compounds of the general formula (I)

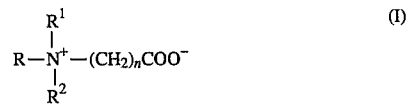

is added to the reaction mixture before or during the quaternization reaction; wherein R, $R^1$, $R^2$, are each $C_1$–$C_{10}$ alkyl, optionally substituted with hydroxyl, and n is 1–3.

7 Claims, No Drawings

PROCESS FOR THE PREPARATION OF HIGHLY CONCENTRATED FREE-FLOWING AQUEOUS SOLUTIONS OF BETAINES

BACKGROUND OF THE INVENTION

The invention relates to a process for the preparation of highly concentrated free-flowing aqueous solutions of betaines which contain solids contents of more than 40% by weight, preferably more than 50% by weight.

Betaines have become established in recent years in the cosmetics industry as a regular ingredient of formulations, in particular for hair and body cleansing. They have the ability to form a dense and creamy foam which remains stable over a long period, even in the presence of other surfactants, soaps and additives, associated with cleansing properties which are acknowledged to be good without any irritant side effects, even on sensitive skin.

The preparation of betaines is described in detail in the relevant patent and specialist literature (U.S. application No. 3 225 074). In general, this entails compounds which contain tertiary amine nitrogen atoms being reacted with ω-halo carboxylic acids or their salts in aqueous or water-containing media.

The particularly used compounds which contain tertiary amine nitrogen atoms are fatty acid amides of the general formula (II)

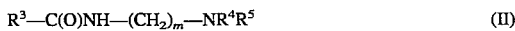

$$R^3-C(O)NH-(CH_2)_m-NR^4R^5 \qquad (II)$$

in which $R^3$ is the hydrocarbon radical of a fatty acid, which radical is alkyl or alkylene, is straight or branched, and can contain optionally one or more, preferably one to five, double bonds and optionally one to five hydroxyl groups, $R^4$ and $R^5$ are identical or different and each is a straight or branched alkyl radical with 1–4 carbon atoms, and m can be 1–3.

In this connection, the alkyl radical $R^3$ can be derived form the natural or synthetic fatty acids with 6–20 carbon atoms, preferably from the natural vegetable or animal fatty acids with 8–18 carbon atoms, as well as their naturally occurring specifically adjusted mixtures with one another or among one another.

Examples of suitable fatty acids are caproic acid, caprylic acid, captic acid, lauric acid, palmitic acid, stearic acid, linoleic acid, linolenic acid and ricinoleic acid.

The naturally occurring fatty acid mixtures with a mixture of chain lengths that can be 8–18 carbon atoms, such as coconut fatty acid or palm kernel fatty acid, which may optionally be hardened by suitable hydrogenation methods, are preferred.

These fatty acids or fatty acid mixtures are converted by conventional condensation reaction techniques at 140°–200° C. with one or more amines of the general formula (III)

$$H_2N-(CH_2)_m-NR^4R^5 \qquad (III)$$

in which $R^4$ and $R^5$ and m have the meaning specified above with respect to the formula (II), to the fatty acid amides with tertiary nitrogen atoms of the general formula (II).

The subsequent quaternization reaction to give betaines of the formula (IV)

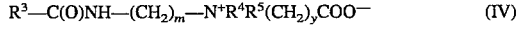

$$R^3-C(O)NH-(CH_2)_m-N^+R^4R^5(CH_2)_yCOO^- \qquad (IV)$$

in which $R^3$, $R^4$, $R^5$ and m have the same meaning as for the formulae (II) and (III) and y can be 1, 2, 3, can be carried out by processes known from the literature.

As a rule, this entails adding to the fatty acid amide of the formula (II) in aqueous medium one or more ω-haloalkylcarboxylic acids, preferably chloroacetic acid, or the salt thereof, preferably the sodium salt, and completing the quaternization in a reaction at about 80°–100° C. for several hours. Depending on the fatty acid or fatty acid mixture used it can be necessary, in order to maintain stirrability as the reaction advances, for a minimum amount of water to be present. The commercially customary concentration of betaine content in the solutions prepared in this way is therefore about 30% by weight or below.

To save storage and transport costs as well as for formulation technological reasons in further processing, however, in many cases a higher concentration has been urgently required.

In the past therefore a number of processes intended to solve this problem have been proposed. Thus, DE-C 3 613 944 discloses a process in which the quaternization is carried out in an organic polar solvent with a water content of 20% by weight, and then the solvent is removed wholly or partly by distillation, and then the desired concentration is adjusted again with an industrially utilizable solvent.

Apart from the fact that the process is industrially elaborate and cost-intensive, organic solvents are in many cases undesired in the further processing to cosmetic formulations.

Although the process disclosed in DE-C 3 726 322 does without organic solvents, the amount of water needed for the quaternization reaction must be removed again from the reaction product by distillation, and the pH of the solution must be adjusted by relatively large amounts of acid to values of 1–4.5, which are untypical of the skin, before or after the adjustment to the desired concentration.

According to EP-A-0 353 580, nonionic, water-soluble surfactants are added to the reaction mixture composed of fatty acid amide and haloalkylcarboxylic acid before or during the quaternization reaction or to the resulting solution of the betaine, in amounts such that the finished solution contains 3–20% by weight of water-soluble surfactants.

This patent discloses that polyoxyethylene ethers are used as the nonionic surfactants and must, for adequate solubility in water, contain 10–250 oxyethylene units.

Polyoxyethylene ethers with relatively high contents of oxyethylene units have, however, proven to be not without problems in respect of their biodegradability.

There has therefore continued to be a need for highly concentrated, free-flowing and pumpable, aqueous solutions of betaines which are free of lower alcohols such as methanol, ethanol, propanol or isopropanol.

SUMMARY OF THE INVENTION

It has now been found, surprisingly, that free-flowing and pumpable aqueous solutions of betaines can be prepared from the reaction mixture of tertiary amine, particularly, fatty acid amido amine, and ω-haloalkylcarboxylic acid or a salt thereof, especially when compounds of the general formula (I)

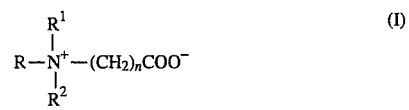

$$\begin{array}{c} R^1 \\ | \\ R-N^+-(CH_2)_nCOO^- \\ | \\ R^2 \end{array} \qquad (I)$$

in which R, $R^1$ and $R^2$, are identical or different straight or branched alkyl radicals having 1–10 carbon atoms which optionally contain hydroxyl groups, in particular methyl radicals, and n is 1–3, preferably n is 1, are added in amounts of 1–5% by weight, preferably 1–4% by weight, based on the complete mixture, to the mixture of the tertiary amine and the ω-haloalkylcarboxylic acid or salt thereof before or during the quaternization reaction.

Preferably, the tertiary amine is a fatty acid amide of the general formula (II) and the ω-halo carboxylic acid is in the form of an alkali metal, preferably sodium, salt of haloalkyl carboxylic acid (Hal)—(CH$_2$)$_y$ COOH wherein (Hal) is fluoride, chloride, bromide, or iodide and y is 1, 2, or 3; most preferred is the sodium salt of chloroacetic acid.

DETAILED DESCRIPTION OF THE INVENTION

Without further concentration operations, solely by appropriate calculation of the water content in the quaternization reaction, the resulting aqueous solutions of betaines are immediately free-flowing and pumpable even without the use of short-chain monofunctional alcohols.

This was all the more surprising since the compounds of the formula (I) which are used according to the invention are predominantly solid or even—like the trimethylglycine or "betaine" which occurs naturally in sugar beet (Beta vulgaris) and is preferably used according to the invention—crystalline.

Further compounds of the general formula (I) which are used according to the invention are quaternization products formed by reacting dimethylethanolamine, methyldiethanolamine or alkyl (C$_2$–C$_{10}$)— diethylamine with monochloroacetic acid.

Even with contents of 5% or less by weight of compounds of the general formula (I) it is possible to obtain free-flowing and pumpable mixtures which contain betaines based on the fatty acid amides of the formula (II) in amounts greater than 45%, in some cases greater than 50%, by weight based on dry matter.

The quaternization is carried out under standard quaternization conditions wherein tertiary amines, preferably those of formula (II), are reacted with the ω-haloalkyl carboxylic acid or salt thereof to from the quaternary compound which preferably has formula (I). The compound of formula (I) is added to the haloacid or salt, or to the tertiary amine, or to the mixture of haloacid and amine. The compound of formula (I) is desired to be present in the quaternization reaction preferably from the beginning of the quaternization.

Since the addition of these compounds does not interfere with the subsequent processing to prepare hair and body cleansers, and they are toxicologically acceptable and undergo biodegradation without problems, it is also possible to use higher contents if desired in the individual case.

The NaCl or other alkali halide content, resulting from the process, in the betaine solution can, as a rule, remain in the solution because it is conventional practice to add electrolyte salts to adjust the viscosity of shampoos or shower gels.

The highly concentrated betaine solutions prepared according to the invention are homogeneous and clear mixtures which are stable over a relatively wide temperature range and which can be diluted to the desired use concentration and compounded without complications for further processing.

A betaine solution prepared according to the instant invention contains

1–5% by weight of one or more compounds of the formula (I);

30–50% by weight of one or more compounds of the formula (IV);

$$R^3—C(O)NH—(CH_2)_m—N^+(R^4)(R^5)—(CH_2)_y COO^- \qquad (IV)$$

wherein R$^3$ is straight or branched alkyl or alkylene containing 6–20 carbon atoms, 0–5 carbon-carbon double bonds and 0–5 hydroxyl substituents, R$^4$ and R$^5$ are identical or different and each is straight or branched alkyl containing 1–4 carbon atoms, m is 1, 2 or 3, and y is 1, 2 or 3;

5–8% by weight of NaCl; and the balance water.

ANALYTICAL METHODS

Dry Matter

The dry matter is determined by drying the material to constant weight at 105° C. These values are determined by the standard methods of the Deutsche Gesellschaft für Fettchemie (DGF): B-II.

Ester Number (EN)

The ester number is a measure of the esters contained in fats and technical fatty acids. It indicates the number of milligrams of potassium hydroxide necessary to hydrolyze 1 gram of substance or technical fatty acids (mg KOH/g). These values are determined by the standard methods of the Deutsche Gesellschaft für Fettchemie (DGF): C-V 4.

Total Amine Number (TAN), Tertiary Amine Number (tAN)

The total amine number indicates the number of milligrams of potassium hydroxide equivalent to the total basicity of 1 gram of the amine compound (mg KOH/g).

The tertiary amine number indicates the number of milligrams of potassium hydroxide equivalent to the tertiary amine basicity of a gram of the amine compound (mg KOH/g).

The values are determined by the American Oil Chemists Society (A.O.C.S.) Official Method Tf 2a-64.

Sodium Chloride

The sodium chloride content is measured potentiometrically with a reference silver nitrate standard solution. A combined silver chloride electrode is used as electrode. The values are determined by the standard method of the Deutsche Gesellschaft für Fettchemie (DGF) : H-III 9.

EXAMPLES

EXAMPLE 1

(a) Preparation of the Amine Amide 98.0 kg of palm kerneloil was mixed with 56.8 kg of dimethylaminopropylamine in a reactor with stirrer, thermometer and distillation head under an inert gas atmosphere and heated to 150°–160° C. and boiled under reflux. After the amidation was complete (ester number <10 mg KOH/g), the excess amine was distilled off in vacuo at this temperature. The distillation was considered complete when the difference between the total amine number and the tertiary amine number was less than 3 mg KOH/g. The resulting amine amide had a TAN of 170.6 mg KOH/g, a tAN of 168.6 mg KOH/g and an ester number of 2.8 mg KOH/g.

(b) Quaternization 12.3 kg of monochloroacetic acid solution (80%) was diluted with 37.0 kg of water while cooling in a reactor with stirrer, internal thermometer and pH meter and cautiously neutralized with 8.1 kg of sodium hydroxide solution (50%). After the neutralization, 3.0 kg of trimethylglycine was added to the sodium chloroacetate mixture, and the mixture was heated to 70°–80° C. After addition of 32.5 kg of the amine amide from Example 1 (a), the reaction mixture was stirred at 80°–90° C. During this the pH was kept between 8 and 8.5. A further 800 g of sodium hydroxide (as 50 percent strength solution) in total was required for this. The alkylation was complete after a reaction time of about 8 h. The betaine mixture was allowed to cool to 50° C. and the pH was adjusted to 5.1 with 640 g of 50 percent strength citric acid solution.

The final product was a clear solution of medium viscosity and with a residue on drying of 50.1% and a sodium chloride content of 6.4%.

EXAMPLE 2

(a) Preparation of the Amine Amid 95.0 kg of hardened coconut oil was mixed with 52.8 kg of dimethylaminopropylamine in a reactor with stirrer, thermometer and distillation head under an inert gas atmosphere and heated to 150°–160° C. After the amidation was complete (ester number <10 mg KOH/g), the excess amine was distilled off in vacuo at this temperature. The distillation was considered complete when the difference between the total amine number and the tertiary amine number was less than 3 mg KOH/g. The resulting amine amide had a TAN of 172.8 mg KOH/g, a tAN of 170.6 mg KOH/g and an ester number of 3.0 mg KOH/g.

(b) Quaternization 12.1 kg of monochloroacetic acid solution (80%) was diluted with 45.0 kg of water while cooling in a reactor with stirrer, internal thermometer and pH meter and cautiously neutralized with 8.1 kg of sodium hydroxide solution (50%). After the neutralization, 1.5 kg of trimethylglycine was added to the sodium chloroacetate mixture, and the mixture was heated to 70°–80° C. After addition of 31.5 kg of the amine amide from Example 2 (b), the reaction mixture was stirred at 80°–90° C. During this the pH of the solution was kept between 8 and 8.5. A further 1000 g of sodium hydroxide (as 50 percent strength solution) in total was required for this. The alkylation was complete after a reaction time of about 8 h. The betaine mixture was allowed to cool to 50° C., and the pH was adjusted to 5.2 with 600 g of 50% strength citric acid solution.

The final product was a clear solution of medium viscosity and with a residue on drying of 45.0% and a sodium chloride content of 6.0%.

What is claimed is:

1. A process for preparing a highly concentrated free-flowing aqueous solution containing 30–50% by weight of one or more betaines of the general formula (IV);

$$R^3-C(O)NH-(CH_2)_m-N^+(R^4)(R^5)-(CH_2)_y COO^- \quad (IV)$$

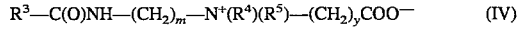

wherein $R^3$ is straight or branched alkyl or alkylene containing 6–20 carbon atoms, 0–5 carbon-carbon double bonds and 0–5 hydroxyl substituents, $R^4$ and $R^5$ are identical or different and each is straight or branched alkyl containing 1–4 carbon atoms, m is 1, 2 or 3, and y is 1, 2 or 3 comprising forming an aqueous reaction mixture containing a compound containing tertiary amine nitrogen atoms of the general formula (II);

$$R^3-C(O)NH-(CH_2)_m-NR^4R^5 \quad (II)$$

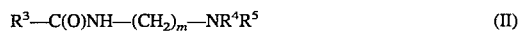

wherein $R^3$, $R^4$, $R^5$ and m have the same meaning as for the formula (IV); one or more haloalkyl carboxylic acids of the formula (Hal)—$(CH_2)_y$COOH wherein (Hal) is fluoride, chloride, bromide or iodide, and y is 1, 2 or 3, and from 1 to 5% by weight of the reaction mixture of at least one compound of the general formula $$R-N^+\begin{array}{c}R^1\\|\\|\\R^2\end{array}-(CH_2)_n COO^- \quad (I)$$

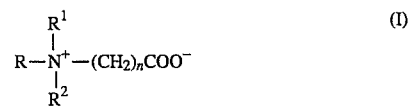

which R, $R^1$, and $R^2$ are identical or different and each is a straight or branched alkyl radical which contains 1 to 10 carbon atoms and which optionally contains a hydroxyl group and n can be 1–3, and subjecting the reaction mixture to quaternization conditions effective to quaternize said one or more compounds which contain tertiary amine nitrogen with said one or more haloalkyl carboxylic acids.

2. A process according to claim 1, characterized in that R, $R^1$) and $R^2$, are $CH_3$ and n is 1.

3. A process according to claim 1, characterized in that R is $CH_3$ or —$CH_2CH_2OH$; $R^1$ and $R^2$ are —$CH_2CH_2OH$; and n is 1.

4. A process according to claim 2 characterized in that the one or more compounds of the general formula (I) comprise 1–5% by weight of the reaction mixture.

5. A process according to claim 4 wherein (Hal) is chloride.

6. A process according to claim 1, characterized in that said one or more betaines comprises one or more 1-alkanoylamino-3-dimethylamino-propane- 3-carboxymethyl compounds of the formula $R^3$— C(O)NH—$(CH_2)_3$—$N^+$$(CH_3)_2CH_2COO^-$ wherein $R^3$ is alkyl containing 6 to 20 carbon atoms.

7. A process according to claim 6, wherein said one or more betaines comprises a mixture of compounds of the formula $R^3$—C(O)NH—$(CH_2)_3$—$N^+(CH_3)_2COO^-$ wherein $R^3$ represents a distribution of chain lengths corresponding to the distribution of fatty acid residues in naturally occurring coconut fatty acids.

* * * * *

UNITED STATES PATENT AND TRADEMARK OFFICE
CERTIFICATE OF CORRECTION

PATENT NO. : 5,464,565
DATED : November 7, 1995
INVENTOR(S) : Ingo Hamann, et al.

It is certified that error appears in the above-indentified patent and that said Letters Patent is hereby corrected as shown below:

Column 1, line 20: "application" should read --Application--, and "322074" should read --3,225,074

Column 5, line 16: "Amid" should read --Amide--

Column 6, line 24, Claim 1: before "which" insert --in--

Column 6, line 31, Claim 2: "$R^1$)" should read --$R^1$--

Signed and Sealed this

Second Day of July, 1996

Attest:

BRUCE LEHMAN

Attesting Officer

Commissioner of Patents and Trademarks